United States Patent [19]
Fujimoto

[11] Patent Number: 5,789,680
[45] Date of Patent: Aug. 4, 1998

[54] SACRIFICIAL SPECIMEN FOR USE IN STRUCTURAL MONITORING FOR PREDICTING FATIGUE DAMAGE

[75] Inventor: Yukio Fujimoto, Higashihiroshima, Japan

[73] Assignee: Hiroshima University, Hiroshima, Japan

[21] Appl. No.: 746,626

[22] Filed: Nov. 12, 1996

[30] Foreign Application Priority Data

May 15, 1996 [JP] Japan .................................. 8-120219

[51] Int. Cl.$^6$ .......................... G01N 19/08; G01N 29/04
[52] U.S. Cl. .................................................. 73/719; 73/786
[58] Field of Search ................................. 73/786, 799

[56] References Cited

U.S. PATENT DOCUMENTS

| | | | |
|---|---|---|---|
| 3,979,949 | 9/1976 | Smith | 73/799 |
| 4,107,980 | 8/1978 | Crane et al. | 73/799 |
| 4,164,874 | 8/1979 | Cassatt et al. | 73/799 |
| 4,255,974 | 3/1981 | Dufrane et al. | 73/799 |
| 5,520,055 | 5/1996 | Fussinger | 73/799 |

Primary Examiner—George M. Dombroske
Assistant Examiner—Max H. Noori
Attorney, Agent, or Firm—Oliff & Berridge, PLC

[57] ABSTRACT

A sacrificial specimen for use in monitoring fatigue damage of a structural member including a main body made of the same material of the structural member and having an artificially formed crack at a central region thereof, and first and second thin epoxy resin plates cemented to both surfaces of the main body by an epoxy resin adhesive agent except for the central region. The main body is made by a thin metal plate having a thickness of 0.25 mm. In order to keep the central region of the main body free from the adhesive agent, a synthetic resin film is wound around the central region of the main body. The sacrificial specimen is secured to a surface of the structural member by means of an epoxy resin adhesive agent. A condition of fatigue crack growth at the artificially formed crack is monitored by a microscope, and fatigue crack of the structural member can be predicted from the monitored condition.

9 Claims, 7 Drawing Sheets

FIG_2A
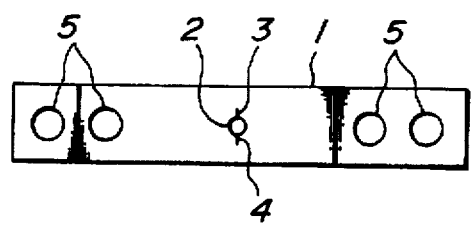
FIG_2B
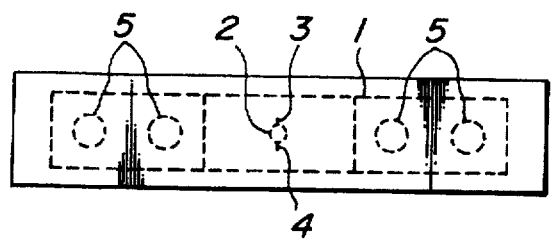
FIG_2C
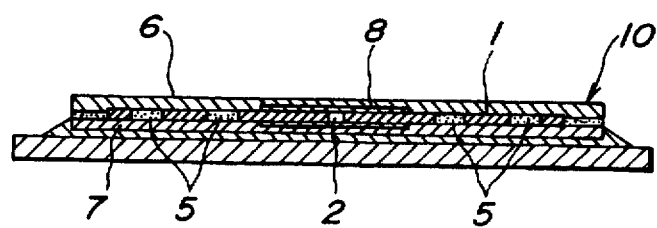

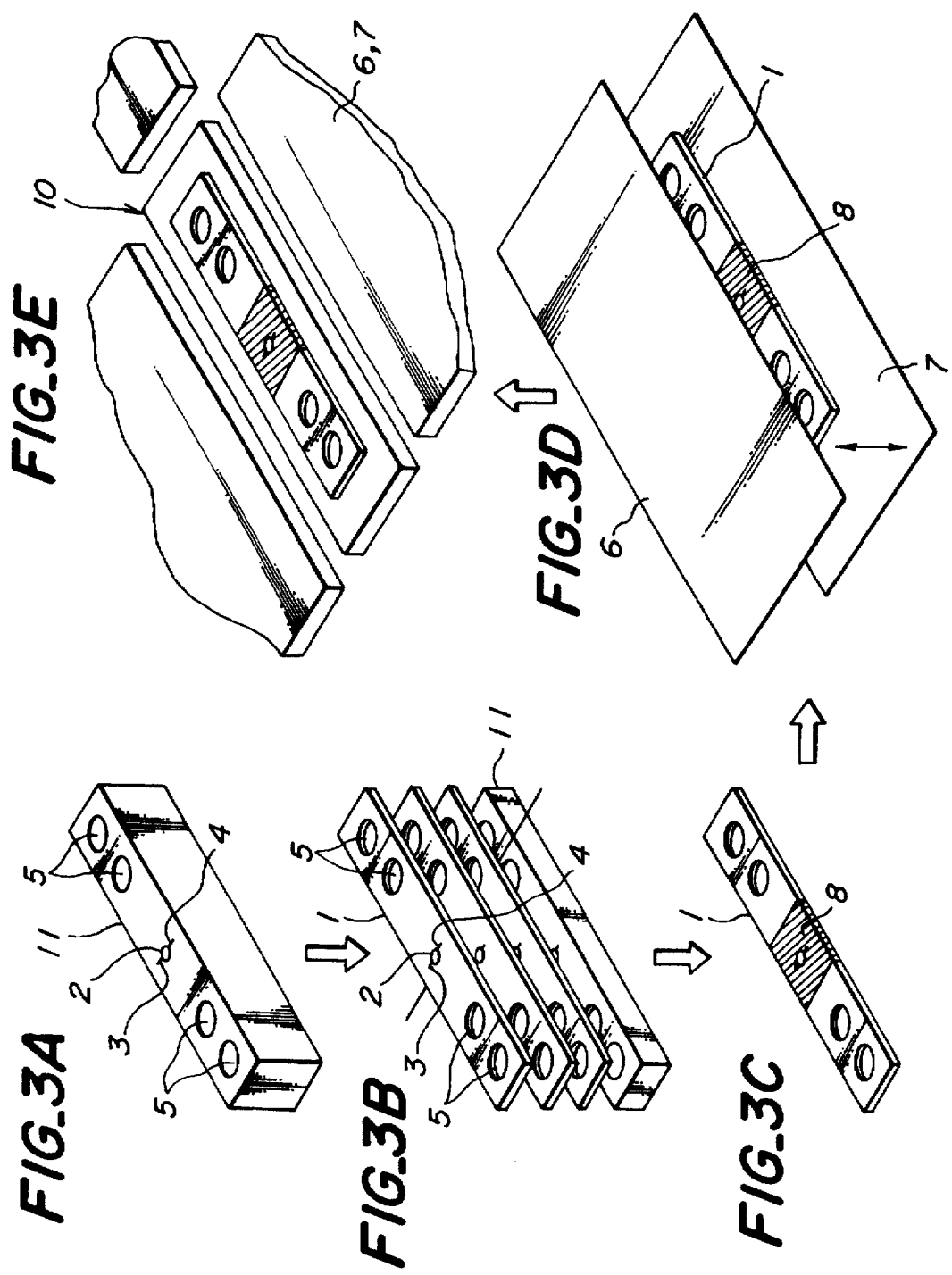

FIG_5A
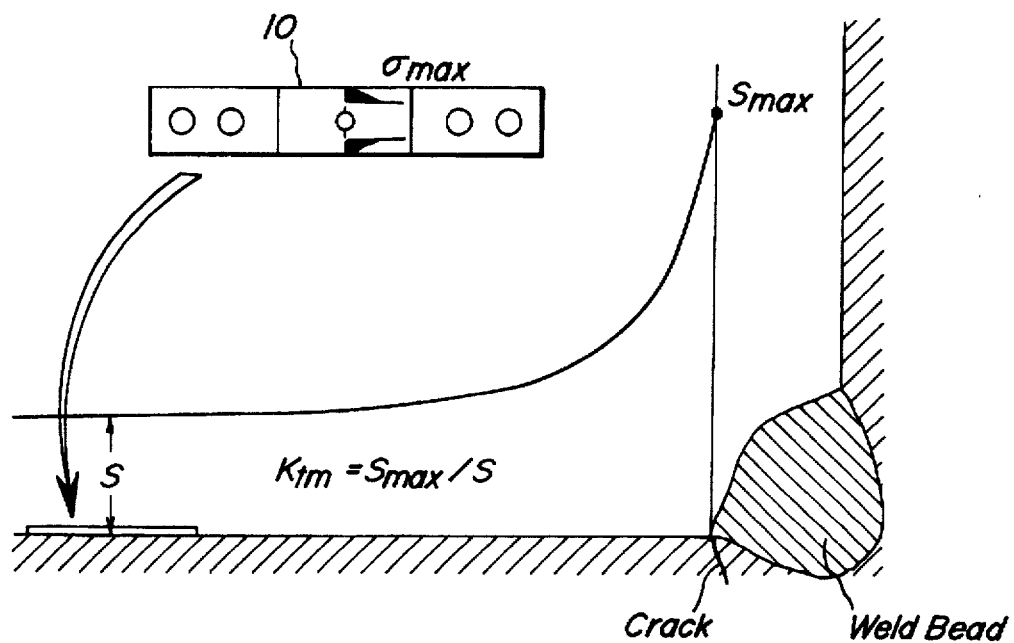
FIG_5B
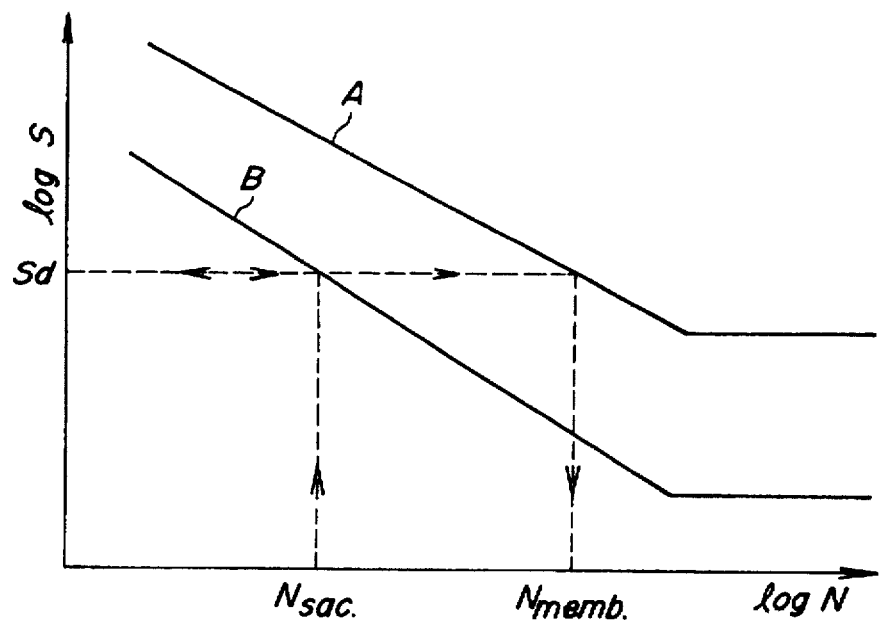

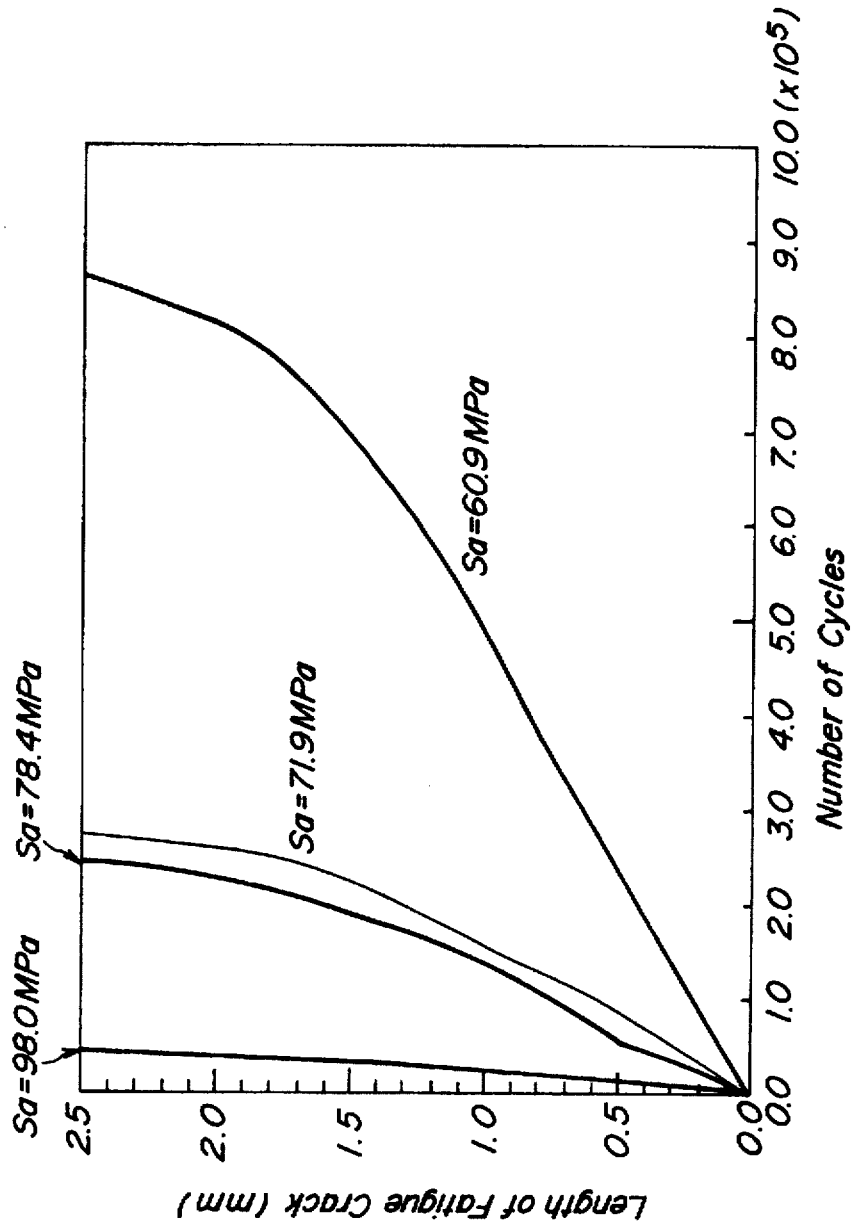

SACRIFICIAL SPECIMEN FOR USE IN STRUCTURAL MONITORING FOR PREDICTING FATIGUE DAMAGE

BACKGROUND OF THE INVENTION

1. Field of the Invention

The present invention relates to a sacrificial specimen for use in a structural monitoring for predicting fatigue damage of structural members. Such a structural monitoring is worth while in attaining a safety of structural members which might be damaged by fatigue.

2. Related Art Statement

In order to keep safety of various structural members such as ships, bridges, railway bridges, iron towers, marine structures, buildings, constructing machines and railway transportation machines, it is very important to predict fatigue damage or cracks of these structural members. Due to a recent progress in structural analysis and structure design method, fatigue designing has been improved day by day. However, there has not been established fatigue designing in which a portion at which fatigue damage will occur can be correctly or reliably predicted. This is due to a fact that fatigue mechanism is very complicated and there are existent various uncertain factors such as uncertainty of external force, precision of structural analysis, working precision and residual force.

Under the above circumstances, in order to improve a safety of structural members, it would be effective to put an effort in safety management of the structural members during usage by investigating actual structural members as well as by a structural monitoring.

FIG. 1 shows a general planning of monitoring of fatigue damage. As shown in FIG. 1, there are a method of detecting fatigue damage or crack and a method of predicting fatigue damage or crack. In the former fatigue crack detection method, the existing fatigue crack in a structural member is detected. This method has been widely practiced for monitoring fatigue damage. However, there are many structural members which could hardly be inspected, and the fatigue crack detection method could not be applied to such structural members. Moreover, in the fatigue crack detection method, there might be introduced inevitable human error, and further a running cost might be increased. In some cases, routine works using structural members have to be interrupted for detecting the fatigue crack.

The fatigue crack prediction method is a method of predicting a possible fatigue crack in a structural member. This prediction method includes various methods. For instance, a method of measuring strain of structural member, a method of microscopically investigating a surface condition of structural member, a method of estimating residual lifetime of a sample cut out of a structural member, and a method of monitoring a condition of a sacrificial specimen provided on a structural member. The strain measuring method has been practically performed for predicting the fatigue crack in a hot spot. However, this method requires an electric power source for a strain gauge and a recorder for recording a history of strain over a rather long time period. Moreover, in this method, the fatigue crack is predicted by using an accumulation damage rule, and thus a reliability of this method depends on a precision of the accumulation damage rule.

In the method of using a sacrificial specimen, a sacrificial specimen is formed to be damaged much more easily than a structural member and is secured to the structural member near a hot spot, and a condition of the sacrificial specimen is monitored. A timing at which fatigue damage might occur in the structural member is estimated on a basis of a detected fatigue damage condition of the sacrificial specimen. This method can not only estimate a life time of a structural member, but also can provide useful information about a history of load and an accumulated damage threshold value. It should be noted that such information is important in judging fatigue of an actual structural member. Moreover, the method of using the sacrificial specimen can provide a new way to an intelligent structural member.

As explained above, the method using the sacrificial specimen will be important in a feature. However, a study of this method has been just begun, and therefore a practically usable sacrificial specimen has not been developed.

SUMMARY OF THE INVENTION

The present invention has for its object to provide a novel and useful sacrificial specimen for use in the fatigue damage monitoring system for predicting a timing at which fatigue damage will actually appear in a structural member on the basis of information obtained by monitoring a fatigue damage condition of the sacrificial specimen fixed to the structural member.

According to the invention, a sacrificial specimen for use in a fatigue damage prediction method comprises:
- a main body in a form of a thin plate made of a material which is identical with that of a structural member whose fatigue damage is to be predicted and includes a center notch at a central region of the thin plate viewed in a longitudinal direction; and
- first and second synthetic resin plates cemented to opposite surfaces of said main body at areas except for said central region of the main body such that said main body is sandwiched between said first and second synthetic resin plates.

In a preferable embodiment of the sacrificial specimen according to the invention, said main body has a thickness of about 0.25 mm.

In case of securing sacrificial specimens onto structural members, there have been proposed various methods such as bolt coupling, welding and cementing. In the bolt coupling and welding, there might be produced an undesired concentration of stress in the structural member. Moreover, a residual stress might be produced at a time of coupling or welding. Whilst, the cementing method does not give substantial influence on the structural member and thus is superior to the bolt coupling method and welding method. However, the cementing method includes the following problems which have prevented the cementing method from being practically used.

[Problem of Cementing Strength]

Since the sacrificial specimen has to be provided in a vicinity of a hot spot, it is desired to reduce a size of the sacrificial specimen as small as possible. When a small sacrificial specimen is used, a magnitude of load which could be propagated to the sacrificial specimen through a cementing region might be restricted. As a result thereof, a mechanical strength of the cementing region becomes too small, and the sacrificial specimen is liable to be peeled from the structural member.

[Problem of Monitoring Period]

In order to mitigate the above mentioned problem, a cross sectional area of the sacrificial specimen may be decreased. However, then stress could not be concentrated effectively and a time period from a fatigue crack growth to a breakage of the sacrificial specimen might be shortened. Therefore, a monitoring time period might be restricted.

[Problem of Accumulated Fatigue Damage Rule]

If a sacrificial specimen is made of a material different from a material of a structural member whose fatigue damage is to be predicted, it is difficult to predict a life time of the structural member from date obtained by monitoring the sacrificial specimen due to difference in fatigue characteristics between the structural member and the sacrificial specimen.

[Problem of Buckling]

To a sacrificial specimen are subjected to both compressive strain and tensile strain. When the sacrificial specimen is compressed, there might occur a problem of buckling. It is difficult to provide a sacrificial specimen which can effectively resist against buckling.

The inventor of the present application has conducted various experiments and analyses and has succeeded to develop a novel and useful sacrificial specimen which can solve or at least mitigate the above mentioned various problems. A principal conception in developing the sacrificial specimen according to the present invention may be summarized as follows:

(1) The main body of sacrificial specimen according to the invention is made of the same material as that of a structural member to which the sacrificial specimen is to be secured, and thus fatigue characteristics of the specimen can be made identical with those of the structural member.

(2) The sacrificial specimen is secured to the structural member by means of cementing using an adhesive agent, and a surface of the specimen which is to be brought into contact with the structural member has no protrusions and depressions.

(3) A cross sectional area of the sacrificial specimen is sufficiently reduced such that a cementing region could not be peeled off. At the same time, the sacrificial specimen could be prevented from buckling.

(4) Although a cross sectional area of the sacrificial specimen is small, it is possible to highly concentrate stress, and a fatigue crack is produced at an earlier time than in a hot spot.

(5) In order to monitor a progress of fatigue crack in the sacrificial specimen, the sacrificial specimen is formed as a crack propagation type. Moreover, in order to investigate a progress of fatigue crack of the sacrificial specimen without fail for a long time period, a long crack propagation time period can be attained.

(6) The sacrificial specimen has a simple configuration so that stress concentration factor and stress intensity factor can be calculated easily.

BRIEF DESCRIPTION OF THE DRAWINGS

FIGS. 2A–2C illustrate an embodiment of the sacrificial specimen according to the invention;

FIGS. 3A–3E are perspective views depicting a method of manufacturing the sacrificial specimen according to the invention;

FIGS. 5A and 5B are schematic diagram and graph for explaining a manner of predicting a fatigue damage timing of a structural member by using the sacrificial specimen according to the invention;

FIG. 7 is a graph showing a progress of fatigue crack growth in the sacrificial specimen.

DESCRIPTION OF THE PREFERRED EMBODIMENT

Figure 1:
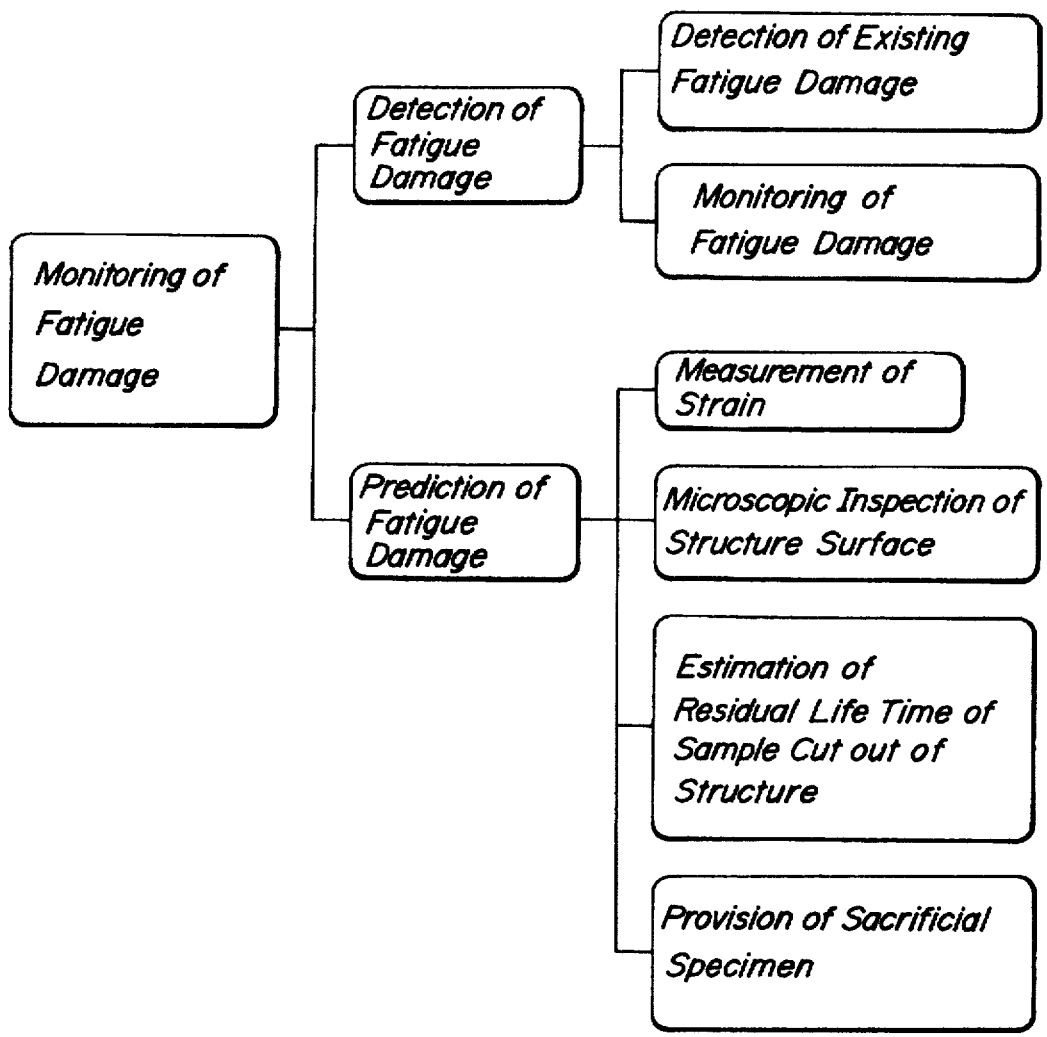
FIG. 1 is a diagram showing a planning of fatigue damage monitoring.

FIGS. 2A–2C show an embodiment of the sacrificial specimen according to the invention. FIG. 2A is a plan view showing a main body of the sacrificial specimen, and FIGS. 2B and 2C are plan and cross sectional views, respectively, of the sacrificial specimen. The main body 1 of the sacrificial specimen shown in FIG. 2A is formed by a thin metal plate made of the same material as that of a structural member whose fatigue damage is to be predicted. Therefore, fatigue characteristics such as accumulated fatigue damage threshold value of the sacrificial specimen can be made identical with those of the structural member. In the present embodiment, the main body 1 is made of a mild iron SS41. In order to generate fatigue crack in the sacrificial specimen at a much more early timing than in the structural member, the main body 1 has formed therein a stress concentration region. That is to say, a small circular hole 2 having a diameter of 2.5 mm is formed at a central region of the main body 1 and a pair of artificial cracks 3 and 4 which extend from the circular hole 2 in opposite directions which are perpendicular to a longitudinal direction of the main body. Each of the artificially formed cracks 3 and 4 has a width of 0.1 mm and a length of 1.25 mm.

According to the invention, it is necessary to make a thickness of the main body 1 of the sacrificial specimen sufficiently small. In the present embodiment, the main body 1 is formed by a thin plate having a thickness of about 0.25 mm. By reducing a thickness of the main body 1, it is possible to reduce a shearing stress applied to a cementing region by means of which the sacrificial specimen is secured to a structural member. Furthermore, according to the invention, the main body 1 of the sacrificial specimen has to be sufficiently small. In the present embodiment, the main body 1 has a length of 60 mm and a width of 10 mm.

As illustrated in FIG. 2A, near respective ends of the main body 1 there are formed two circular holes 5. As will be explained later, these holes 5 serve to promote a coupling of the main body with synthetic resin plates upon cementing these parts with an adhesive agent. That is to say, the adhesive agent is introduced into the holes 5 to constitute coupling pins.

As shown in FIGS. 2B and 2C, the main body 1 is sandwiched between two thin epoxy resin plates 6 and 7 and these parts are cemented together by means of an adhesive agent. In the present embodiment, the adhesive agent is made of epoxy resin, but according to the invention, any other adhesive agent may be used as long as the main body 1 and epoxy resin plates 6 and 7 can be firmly fixed together to obtain a final sacrificial specimen 10. Upon assembling the main body 1 and epoxy resin plates 6 and 7, care should be taken that the central region of the main body in which the cracks 3 and 4 are formed is not cemented to the plates 6 and 7, so that the central region of the main body can be freely deformed. To this end, a very thin transparent fluorine-contained resin film 8 is wound around the central portion of the main body 1. In the present embodiment, the film 8 is made of a polytetrafluoro-ethylene (Teflon: trade name) and has a width of 20 mm. The epoxy resin adhesive agent could not be adhered to the Teflon film 8, and therefore the central region of the main body 1 can be free from the adhesive agent. According to the invention, a polyethylene film may be used instead of the Teflon film or a mold release may be applied to the central region of the main body 1.

By sandwiching the main body 1 between the epoxy resin plates 6 and 7 each having a thickness of 0.25 mm, the sacrificial specimen 10 can be effectively prevented from buckling even if a compressive force is applied thereto. Moreover, the sacrificial specimen 10 can be easily handled. In the present embodiment, the synthetic resin plates 6 and 7 are made of epoxy resin, but according to the invention any other transparent or translucent synthetic resin having a sufficient mechanical strength may be equal used.

The sacrificial specimen 10 of the present embodiment has a length of 70 mm, a width of 20 mm and a thickness of 1.0 mm.

Now the method of manufacturing the sacrificial specimen shown in FIG. 2C will be explained with reference to FIGS. 3A–3E.

At first, a block 11 made of the same material as that of a structural member is prepared. In the present embodiment, the block 11 is made of a soft iron SS41. The block 11 has the same length and width as those of the main body 1 of the sacrificial specimen but its thickness is larger than that of the main body 1. In this block 11 there are formed small central hole 2, artificial cracks 3, 4 and large holes 5 as illustrated in FIG. 3A. Then, the block 11 is sliced by a wire cutter as shown in FIG. 3B to obtain a plurality of main bodies 1. Surfaces of these main bodies 1 are polished by using an emery paper.

Next, a central region of a main body 1 is wound by a transparent Teflon film 8 as depicted in FIG. 3C. Then, the main body 1 having the Teflon film 8 wound thereon is sandwiched between a pair of thin transparent or translucent epoxy resin plates 6 and 7 as shown in FIG. 3D, and these parts are cemented together. In this case, it is preferable to use an epoxy resin adhesive agent, but according to the invention, other adhesive agent may be used as long as a required mechanical strength can be attained.

After drying the adhesive agent, the epoxy resin plates 6 and 7 are cut out to obtain the sacrificial specimen 10 as illustrated in FIG. 3E. By cementing the main body 1 between the thin epoxy resin plates 6 and 7, the sacrificial specimen 10 can be secured to the structural member without being sagged, can be effectively prevented from being buckled, and can be handled easily. A length, width and thickness of the sacrificial specimen 10 are about 70 mm, 20 mm and 1.0 mm, respectively.

In order to monitor fatigue damage of the sacrificial specimen to predict a timing at which fatigue crack might be produced in a structural member, the sacrificial specimen is adhered onto a surface of the structural member near a hot spot thereof. For this purpose, an epoxy resin adhesive agent may be advantageously used, but according to the invention, any other adhesive agent may be utilized as long as a given mechanical strength can be attained in a cementing region between the sacrificial member and the structural member. A fatigue crack growth at the artificially formed cracks 3 and 4 is monitored through the transparent or translucent epoxy resin plate 6 by means of a microscope.

It should be noted that stress propagation factor and stress concentration factor of the sacrificial specimen may be changed or adjusted by changing various parameters of the sacrificial specimen such as a size, a length of the artificially formed cracks 3 and 4, a length of the central region of the main body 1 around which the Teflon film 8 is wound and thicknesses of the epoxy resin plates 6 and 7. By suitably setting these parameters, it is possible to realize a sacrificial specimen having desired characteristics. For instance, the longer a length of the central region around which the Teflon film 8 is wound is, the sooner fatigue crack growth appears. If a thickness of the epoxy resin plate 7 which is brought into contact with the structural member is large, a stress propagation factor becomes too small. In the present embodiment, a stress propagation factor of 92–93% can be realized.

Figure 4:
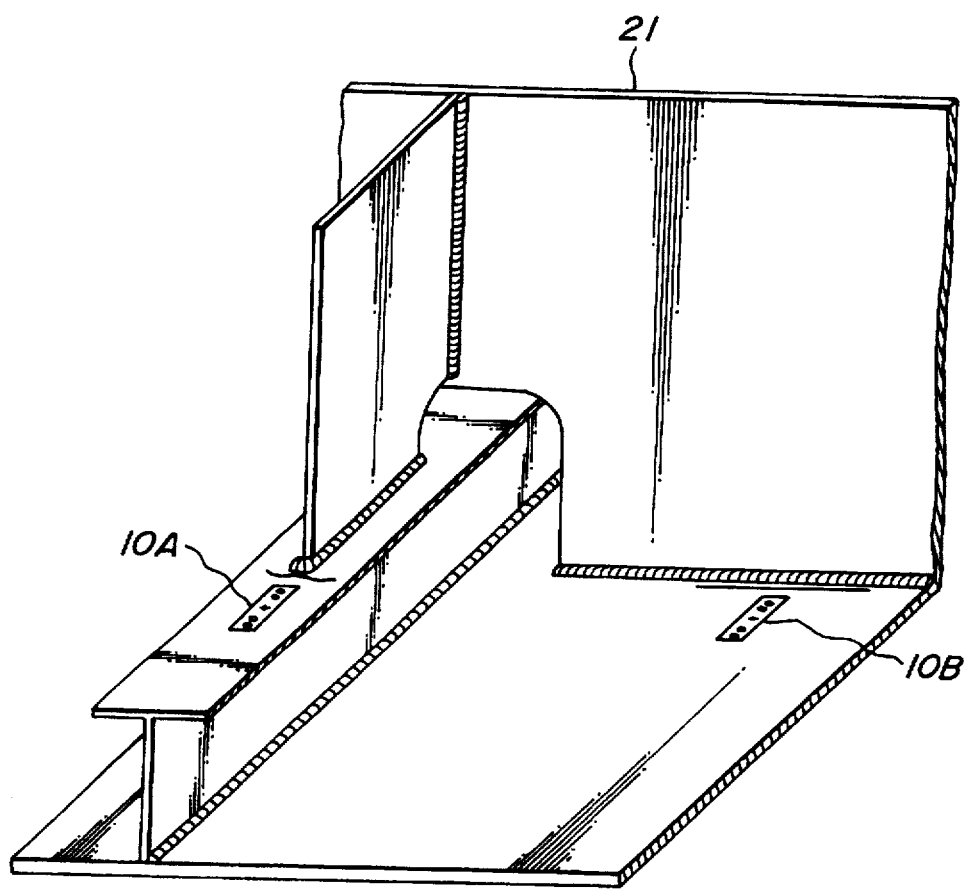
FIG. 4 is a perspective view showing a manner of securing the sacrificial specimens to a structural member.

Now a method of predicting the fatigue damage of a structural member by using the sacrificial specimen according to the invention will be explained. Sacrificial specimens designed to have a life time which is sufficiently shorter than that of the structural member are prepared. In the present experiment, the sacrificial specimens have a life time of a half or one year. These sacrificial specimens are secured to the surface of the structural member whose fatigue damage is to be predicted. As shown in FIG. 4, sacrificial specimens 10a and 10b are secured to a surface of a structural member 21 at positions in the vicinity of hot spots at which a stress gradient is abruptly changed. By providing the sacrificial specimens 10a and 10b at such positions, a precision of estimating a stress at the specimen fixing positions can be improved.

Now a method of predicting fatigue damage of the structural member 21 by monitoring a monitored fatigue damage condition of a sacrificial specimen will be explained also with reference to FIGS. 5A and 5B.

As shown in FIG. 5A, a stress propagated to a position of the structural member at which the sacrificial specimen 10 is secured is denoted by S and a maximum stress produced at a hot spot, i.e. an edge of a weld bead is represented by $S_{max}$. Then, a stress concentration factor $K_{tm}$ is defined to be expressed by $K_{tm}=S_{max}/S$. If a magnitude of a stress applied to a tip of an artificially formed crack is larger than $S_{max}$, a crack growth is initiated earlier than in the structural member.

The stress concentration factor $K_{tm}$ can be previously known from the structural analysis and a strain measurement. Further, an S-N curve (Stress-Number of cycles) of the structural member is predicted as shown by a curve A in FIG. 5B. An S-N curve of the sacrificial specimen is measured by providing the sacrificial specimen onto a flat test or standard member. A curve B in FIGS. 5B shows the thus measured S-N curve of the sacrificial specimen.

When the number of cycles $N_{sac}$ of application of load at which fatigue damage appears in the sacrificial specimen is first detected. Then, a stress Sd corresponding to the thus detected number of cycles $N_{sac}$ is read from the S-N curve B. Next, a life time $N_{memb}$ at which fatigue crack might be produced in a vicinity of the hot spot of the structural member can be predicted from the S-N curve A of the structural member.

Figure 6:
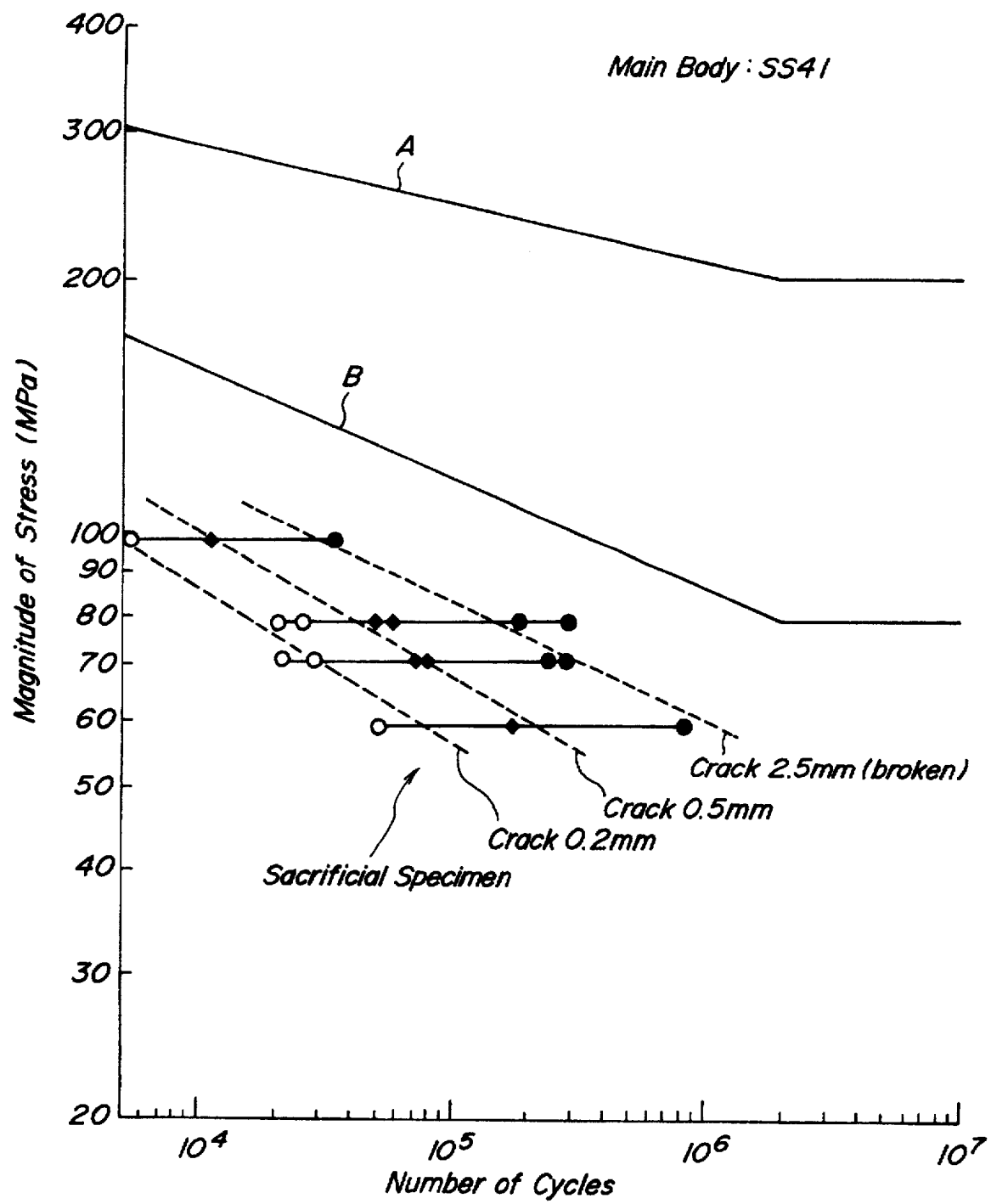
FIG. 6 is a graph representing an S-N curve of the sacrificial specimen.

FIG. 6 shows S-N curves obtained by performing an axial force fatigue test by applying a given magnitude of stress to a sacrificial specimen secured onto a rectangular structural member having no cut-out portion. Compressive stress and tensile stress having the same stress magnitude are alternatively applied to the sacrificial specimen in a cyclic manner. In FIG. 6 there are also shown S-N curves A and B of the above mentioned rectangular standard member on which the sacrificial specimen is secured and a rectangular plate whose sides are cut-out locally to have a stress concentration factor of 3.0 are also shown for the sake of comparison.

From FIG. 6, it can be understood that when the sacrificial specimen having a stress concentration factor of about 5 is secured to the standard member at a position having $K_{tm}$ of 3-4, fatigue crack is produced in the sacrificial specimen at a timing sufficiently earlier than in the structural member, and thus a life time of a hot spot can be predicted. Moreover, it can be understood that after a fatigue crack having a length of 0.2 mm has been produced in the sacrificial specimen, the sacrificial specimen could not be broken for a rather long time period. Therefore, it is possible to attain a sufficiently long monitoring period by using the sacrificial specimen according to the invention. Further, during the fatigue test, the sacrificial specimen has not been peeled from the structural member and could be prevented from being buckled.

FIG. 7 show crack growth curves of the sacrificial specimens according to the invention under various stress magnitudes Sa.

As explained above in detail, in the sacrificial specimen according to the invention, although a cross sectional area of the sacrificial specimen is small, sufficiently large stress concentration can be attained, and a sufficiently long monitoring time period can be obtained from a generation of fatigue crack to a breaking. Moreover, the sacrificial specimen can be effectively prevented from being buckled under a compressive strain. Therefore, by providing the sacrificial specimen according to the invention onto a structural member and by monitoring a fatigue damage condition of the sacrificial specimen, a life time of the structural member can be precisely and reliably predicted. For instance, when a residual life time of the sacrificial specimen is monitored to be a half year, then a structural member can be predicted to have a residual lifetime of, for instance five years, which is ten times longer than that of the sacrificial specimen.

In this manner, by using the sacrificial specimen according to the invention, a timing at which fatigue crack is produced in a structural member can be predicted precisely and reliably, and thus a safety of the structural member can be attained. Furthermore, the monitoring data obtained by inspecting the sacrificial member may be advantageously utilized in a feature fatigue designing.

It should be noted that the even after the main body of the sacrificial specimen is broken, the resin plates are not damaged, and broken surfaces of the main body can be kept clean. Therefore, the broken surfaces can be inspected accurately and precisely, and by performing a striation interval measurement, a history of load to the sacrificial member can be also predicted.

The present invention is not limited only to the embodiment explained above, but many alternations and modifications can be conceived by those skilled in the art within the scope of the invention.

What is claimed is:

1. A sacrificial specimen for use n a fatigue damage prediction method comprising:

a main body in a form of a thin plate made of a material which is identical with that of a structural member whose fatigue damage is to be predicted and includes at least one artificially formed crack at a central region of the thin plate viewed in a longitudinal direction; and first and second synthetic resin plates cemented by an adhesive agent to opposite surfaces of said main body at areas except for said central region of the main body such that said main body is sandwiched between said first and second synthetic resin plates.

2. A sacrificial specimen as claimed in claim 1, wherein said main body has a thickness of about 0.25 mm.

3. A sacrificial specimen as claimed in claim 2, wherein said main body has a length of about 60 mm and a width of about 10 mm and a pair of said artificially formed cracks are formed on opposite sides of a hole.

4. A sacrificial specimen as claimed in claim 3, wherein each of said artificially formed cracks has a length of about 1.25 mm and a width of about 0.1 mm.

5. A sacrificial specimen as claimed in claim 4, wherein said first and second synthetic resin plates are made of transparent or translucent epoxy resin.

6. A sacrificial specimen as claimed in claim 5, wherein said first and second plates have a thickness of about 0.25 mm.

7. A sacrificial specimen as claimed in claim 5, wherein said adhesive agent is made of epoxy resin.

8. A sacrificial specimen according to claim 1, wherein said sacrificial specimen further comprises a synthetic resin film wound around said central region of the main body such that the central region is free from the adhesive agent.

9. A sacrificial specimen as claimed in claim 1, wherein said main body has holes formed on both sides of said central region such that said adhesive agent is introduced into said holes.

* * * * *